United States Patent [19]

Struble et al.

[11] 4,147,771

[45] Apr. 3, 1979

[54] ATTRACTANT FOR ARMY CUTWORM MOTHS

[75] Inventors: Dean L. Struble; G. Edward Swailes, both of Lethbridge, Canada

[73] Assignee: Canadian Patents and Development Limited, Ottawa, Canada

[21] Appl. No.: 916,227

[22] Filed: Jun. 16, 1978

[30] Foreign Application Priority Data

Jun. 22, 1977 [CA] Canada .................................. 281126

[51] Int. Cl.$^2$ ............................................ A01N 17/14
[52] U.S. Cl. ..................................................... 424/84
[58] Field of Search ......................................... 424/84

[56] References Cited

U.S. PATENT DOCUMENTS 4,107,293  8/1978  Swailes et al. ......................... 424/84

OTHER PUBLICATIONS

Beroza, "Pest Management With Insect Sex Attractants," A.C.A. Symposium 23, Amer. Chem. Soc., Wash. D.C. (1976) p. 162.
Science, vol. 181, pp. 661–663 (1973).

Primary Examiner—Donald B. Moyer
Attorney, Agent, or Firm—Alan A. Thomson

[57] ABSTRACT

An attractant mixture for male moths of the army cutworm Euxoa auxiliaris (Grote) is described. The attractant is based upon a mixture of Z-5-tetradecen-1-yl acetate and E-7-tetradecen-1-yl acetate, in ratios within the range of about 1/99 to about 20/80, preferably 5/95 to 10/90. The attractant is specific for this species and is useful for trapping and monitoring purposes. Attractant inhibitors are also described.

5 Claims, No Drawings

ATTRACTANT FOR ARMY CUTWORM MOTHS

FIELD OF THE INVENTION

An artifical sex pheromone-type of attractant for male moths of the army cutworm *Euxoa auxiliaris* has been developed. The attractant is specific for this species and enables the population of this species to be accurately monitored. The army cutworm occurs throughout western North America and the larvae feed on numerous crops including cereals, alfalfa, mustard, sugar beets, flax and turnips.

BACKGROUND AND PRIOR ART

Recently sex attractants for a number of crop insect pests have been described in the literature. The active compounds are usually $C_{10}$ to $C_{16}$ acetates, alcohols or aldehydes, frequently with one or more double bonds being present (unsaturation). Some of these compounds have been tested only in laboratory tests with only one species present. Not all of these attractants are effective field attractants for one species only. Some compounds or mixtures will exhibit mild attractancy for several species but it is more important and useful to develop an attractant system which is specific for only one species. Even though artificial attractants have recently been found for several cutworm or armyworm species, it is impossible to predict what a species-specific field attractant for another species will be. Extensive trial-and-error testing in the field is required and the results cannot be predicted. Laboratory olfactometer or electroantennogram tests can serve as a preliminary screen but the results do not indicate the composition of a species-specific field attractant. Artificial field attractants discovered in this way do not necessarily coincide with the actual pheromone produced by the female moths.

The army cutworm, *Euxoa auxiliaris* (Grote), is a pest throughout the semiarid region of the Great Plains of the United States, in the Rocky Mountains and adjacent areas in the United States and Canada.

To our knowledge, nothing has been reported concerning an adult sex pheromone or an adult sex attractant for this species.

Light traps are the only present method of trapping the moths. The light trap attracts many species of moths that are flying at the same time as the army cutworm, and this makes it difficult or impossible to identify the pest species. The light traps are inefficient as only a few moths are captured when there are large numbers in the field. Light traps are expensive to purchase and operate, and they could never be used efficiently for monitoring the population density or for control of this pest.

The life cycle of the army cutworm has been reported and there is one generation per year (Crumb 1929, Walkden 1942, 1950). Blacklight trap records show that there is a flight of newly emerged moths about June and a second flight in August to October (Walkden 1942). Oviposition occurs during the second flight (Pruess 1967). The long interval between emergence and oviposition has been ascribed to a form of estivation (Seamans 1927). Pruess (1967) suggested, however, that the moths migrate to cooler mountainous areas during this period where they actually remain active. The exact time of mating under natural conditions has not been established.

It is desirable to have an adult male attractant that could be used to determine the population densities and habits of the moths and so predict larval infestations and outbreaks.

SUMMARY OF THE INVENTION

A species-specific attractant mixture for adult male moths of the army cutworm has been developed by laboratory and field testing of pure compounds and mixtures. The invention includes an attractant composition for male moths of the army cutworm *Euxoa auxiliaris* (Grote) comprising (a) Z-5-tetradecen-1-yl acetate and (b) E-7-tetradecen-1-yl acetate in ratios of (a)/(b) within the range of about 1/99 to about 20/80. Preferably the ratio of (a)/(b) is from about 5/95 to about 10/90. The attractant was more effective than unmated females in attracting male moths. Either compound (a) or (b) alone was relatively non-attractive to the male moths in the field.

It has also been discovered that two compounds Z-7-tetradecen-1-yl acetate, or Z-7-tetradecen-1-ol strongly inhibited the moth attractant. Only low concentrations of these compounds were required to inhibit attraction, e.g., from about 1% to about 10% relative to the attractant. These inhibitor compounds could be useful to interrupt the normal chemical communication between the male and female moths and thus hinder mating. For instance, when Z-7-tetradecen-1-yl acetate was emitted from a dispenser separate from the attractant dispenser, the attraction of males was observed to be inhibited.

DETAILED DESCRIPTION AND TEST RESULTS

Male army cutworm moths were exposed, in laboratory olfactometers, to 19 $C_{10}$ to $C_{16}$ mono-olefinic acetates. One compound tested, Z-5-tetradecen-1-yl acetate, repeatedly elicited sexual responses from the male moths. This compound alone was not an efficient attractant under field conditions.

At least 100 single compounds and 400 binary combinations were then tested in the field for attractancy for the army cutworm male moths. The compounds were purified n-decyl to n-hexadecyl mono- or di-olefinic acetates and alcohols, and saturated acetates and alcohols. Some compounds were commercially available and others were synthesized by the same general series of reactions as reported by Struble and Swailes in Envir. Entomol. 4:632–636 (1975).

The traps used in the field tests, unless otherwise stated, were of generally cylindrical shape with conical screen funnel entrances at each end. The test compounds were inserted on carriers at the centre of each cylinder. Usually the carriers were rubber bands (e.g., No. 10) but a plastic cap was also found satisfactory. Screen shields were sometimes used around the carriers. The traps were most suitably mounted in the field about 1 m. above ground with one opening facing the prevailing wind. The amount of attractant per trap may range from about 50 to about 1000 micrograms with about 200 micrograms preferred.

Some of the combinations that attracted males are summarized in Table 1. A combination of Z5-14:Ac and E7-14:Ac in ratios of 1/4 and 1/10 attracted the army cutworm males specifically and consistently. Combination of other chemicals with Z5-14:Ac were much less effective. Binary combinations of E7-14:Ac with Z5-12:Ac, Z5-13:Ac, Z5-15:Ac, and Z5-16:Ac at ratios of 4/1 each attracted less than 3 males during September 1975. Many other binary combinations of monoolefinic acetates, and monoolefinic acetates and alcohols attracted less than 10 army cutworm males each, in 1975. An unbaited trap did not capture any males in 1974 and 1975.

Combinations of Z5-14:Ac and E7-14:Ac were effective male attractants, so replicated tests were done to determine the ratio of the 2 components that would attract the most males (Table 2). For the flight period of September 5, to October 2, 1975, the catches increased linearly (P<0.01) as the quantity of E7-14:Ac increased, with the greatest catches to ratios of 8/92 and 11/89. Either chemical alone was essentially non-attractive. In a similar test from September 13 to October 2, 1975, the mean catches did not differ (P>0.05) by regression analysis, but the ratio of 5/95 and 9/91 captured the greatest number of males. Two similar tests were done in 1976 (Table 3) and again the catches of males increased linearly (P<0.01) as the quantity of E7-14:Ac increased to 95 and 94%. The catches decreased when E7-14:Ac was at 99%. It was concluded that Z5-14:Ac and E7-14:Ac in ratios of 1/99 to 11/89 were good attractants and the optimum ratio was about 5/95 to 10/90, with ratios of up to 20/80 operative.

To further optimize the capture of males, the attractant, Z5-14:Ac and E7-14:Ac at a ratio of 5/95, was tested at 4 quantities per rubber band dispenser (Table 4). There was a curvilinear response (P<0.05) between the quantity of attractant and the trap catches with the greatest catches of males to 1.0 mg. per dispenser. The attractant at 0.2 and 3.0 mg. per dispenser were also effective throughout the test period in this trap design. The relative efficiencies of rubber bands and septa as dispensers were compared with the attractant at 1 mg. (Table 4). The greatest numbers of males (P<0.01) were attracted to the rubber band dispensers. The surface containing the attractant was more exposed on the rubber bands than on the septa and presumably this permitted the release of a greater concentration of attractant.

The effectiveness of the attractant was compared to laboratory-reared unmated females. Traps were baited with Z5-14:Ac and E7-14:Ac in a ratio of 8/92 at 200 micrograms per rubber band dispenser or with 1 unmated female. About 58 times more males were attracted to the chemicals than to the females (Table 5). The natural females may be more effective in attracting males, but the laboratory-reared females were aged under conditions that were conducive to pheromone production. It was concluded that the synthetic attractant was very effective, even though the optima ratio and quantity per dispenser may not have been used in this test.

The synergistic and inhibitory effects of other chemicals were determined by adding them to the attractant and comparing the relative trap catches. Various ratios of Z5-14:Ac and E7-14:Ac were used in these tests because their optimum ratio had not been established when these tests were initiated. None of the components tested in 1975 had any significant (P>0.05) synergistic effect on the attractant (Table 6). On the other hand, low percentages of Z7-14:Ac or Z7-14:OH inhibited (P<0.05) the attraction of males. In a later test, 4.4% and 8.4% of Z7-14:Ac in the attractant essentially inhibited the attraction of males (Table 7). This clearly illustrated that E7-14:Ac in the attractant must not contain any of its geometrical isomer Z7-14:Ac. This can be accomplished in the synthesis of E7-14:Ac by reducing the appropriate acetylenic intermediate with sodium in liquid ammonia (see Struble and Swailes reference above), or by resolving mixtures of the geometrical isomers by argentation column chromatrography.

In 1976, E7-14:Ac and 2-(5-tetradecynyloxy)tetrahydropyran, a precursor of Z5-14:Ac, were obtained through a custom synthesis (Raylo Chemical Co.). The E7-14:Ac and the resulting Z5-14:Ac were purified by distillation, and argentation column chromatography followed by preparative gas chromatography. The trap catches to combinations of these chemicals at each degree of purity were compared to the purified (>99%) chemicals synthesized in our laboratory. The mean catches did not differ (P>0.05) (Table 8). During the syntheses of Z5-14:Ac and E7-14:Ac, various percentages of other compounds such as the following may arise: E5-14:Ac, Z5-14:OH, 5-tetradecynyl acetate ($5^a$-14:Ac), $7^a$-14:Ac, E7-14:OH, 14:Ac and 14:OH. These compounds could all occur in the distilled products as they all have similar boiling points. Various percentages of these were added to the attractant, but none of these exhibited synergistic or inhibitor effects (P>0.05) (Tables 6, 8 and 9). It was concluded that low percentages of these components would not interfere with the attraction of army cutworm males.

The various ratios of Z5-14:Ac and E7-14:Ac tested from August to October in 1975 and 1976 were very specific for the army cutworm as about 43,000 males were captured and only about 10 specimens were of other species. Preliminary observations during the 2nd week of September indicated that the majority of the trap catches of army males occurred within 2 h after sunset.

The attractant (or inhibitor) may be dispensed alone, or in combination with a carrier. The carrier may be an inert liquid or solid. Examples of suitable carriers are vegetable oils, refined mineral oils, rubbers, plastics, silica, diatomaceous earth, and cellulose powder. We have found it desirable to impregnate a rubber carrier with the attractant, but other modes of dispensing will be apparent to those skilled in the art.

In our laboratory bioassays of the pheromone extracts and attractant chemicals, the male moths would not respond to the pheromone until they were from 28 to 37 days old. In 1976, 5 traps, baited with synthetic attractant Z5-14:Ac and E7-14:Ac at a ratio of 9/91 and 1 mg. per rubber band dispenser, were in the field from June 11 to September 27. The attractant and dispensers were replaced on July 27. The accumulative total army cutworm males captured were 4, 9, 33, 114, 353, and 877 to July 26, August 10, 16, and 23, and September 2 and 27 respectively. Blacklight trap catches indicated flights of army cutworm in early July and again in late August as previously reported for the species. These results provide indirect evidence that the natural males were not receptive to the attractant until their second flight period, when they were about a month old, which correlated with the laboratory bioassays.

Test results from late 1977 are summarized in Table 10. These tests were carried out with 200 micrograms per rubber band dispenser, in three replications. From Table 10 it is evident that E11-14:Ac is able to be used in addition to or, substitute for part of, the E7-14:Ac with very little decrease in attractancy. Thus E11-14:Ac can be used as an optional ternary additive to the Z5-14:Ac+E7-14:Ac mixture. The amounts of E11-14:Ac can range up to about 50% of the E7-14:Ac and the attractancy still be high.

Total catches of army cutworm male moths to Z5-14:Ac in combination with other chemicals in non-replicated tests from Sept. 4-30, and June 11 to Sept. 30, 1976.

| Z5-14:Ac with | Ratios | Total males captured in 1975 | 1976 |
|---|---|---|---|
| E7-14:Ac | 1:4 | 87 | — |
|  | 1:10 | 122 | 189+ |
| E5-14:Ac | 1:10 | — | 34 |
| Z7-12:Ac | 1:4** | 2 | — |
| Z7-14:Ac | 1:10** | 0 | — |
| Z7-16:Ac | 1:4** | 6 | 13 |
| E7-12:Ac | 1:4** | — | 7 |
| E7-16:Ac | 1:4** | 10 | — |
| Z9-12:Ac | 1:4** | — | 28 |
| Z9-14:Ac | 1:4 | 2 | 2 |
|  | 4:1 | 17 | 29 |
| Z9-16:Ac | 1:4 | 41 | — |
|  | 4:1 | 9 | — |
| E9-12:Ac | 4:1 | 15 | — |
| E9-14:Ac | 1:4 | 2 | — |
|  | 4:1 | 27 | 32 |
| E9-16:Ac | 4:1 | 15 | — |
| Z11-14:Ac | 1:4** | 0 | — |
| Z11-16:Ac | 1:4** | 2 | — |
| E11-14:Ac | 1:4** | 3 | — |
| E11-16:Ac | 1:4** | 2 | — |
| Z7-13:Ac | 4:1 | — | 90 |

*In 1976, the ratios were 5:1 and 1:5 rather than 4:1 and 1:4.
**Ratio of 4:1 caught similar numbers of males.
+Average of 2 traps. Chemicals purified by distillation caught 178 males.

| | September 5 to October 2 | | | September 13 to October 2 | |
|---|---|---|---|---|---|
| Ratios | x̄♂/trap/day | ♂♂ | Ratios | x̄♂/trap/day | ♂♂ |
| 0:100 | 0.1 | 3 | 4:96 | 12.3 | 935 |
| 8:92 | 13.1 | 1421 | 5:95 | 12.9 | 993 |
| 11:89 | 12.9 | 1401 | 7:93 | 12.7 | 967 |
| 20:80 | 8.2 | 885 | 9:91 | 12.9 | 999 |
| 50:50 | 1.6 | 179 | 14:86 | 10.3 | 792 |
| 100:0 | 0.1 | 2 | | | |

| | September 13-30 | | | September 17-30 | |
|---|---|---|---|---|---|
| Ratios | x̄♂/trap/day | ♂♂ | Ratios | x̄♂/trap/day | ♂♂ |
| 1:99 | 3.8 | 271 | 0:100 | 0.0 | 0 |
| 5:95 | 5.0 | 349 | 0.5:99.5 | 1.6 | 85 |
| 10:90 | 3.9 | 267 | 1:99 | 2.9 | 159 |
| 15:85 | 2.1 | 152 | 2:98 | 2.9 | 154 |
| 20:80 | 1.6 | 108 | 4:96 | 3.6 | 195 |
| 25:75 | 0.7 | 53 | 6:94 | 3.1 | 166 |
| 30:70 | 0.5 | 37 | 8:92 | 2.0 | 106 |
| 45:50 | 0.1 | 4 | 10:90 | 2.2 | 118 |
| 60:40 | 0.1 | 3 | 12:88 | 1.7 | 94 |
| 90:10 | 0.0 | 0 | 14:86 | 1.0 | 57 |
|  |  |  | 16:84 | 0.8 | 45 |
|  |  |  | 100:0 | 0.0 | 0 |

| Quantity/dispenser (mg) | x̄♂/trap/day | ♂♂ |
|---|---|---|
| Sept. 16 to Oct. 2, 1975 with rubber bands as dispensers. | | |
| 0.2 | 6.1 | 418 |
| 1.0 | 7.5 | 520 |
| 3.0 | 6.1 | 418 |
| 5.0 | 4.6 | 321 |
| Sept. 14-30, 1976 with rubber bands and septa as dispensers. | | |
| 1.0 (bands) | 3.1 | 200* |
| 1.0 (septa) | 1.6 | 107* |

*Means were different (P < 0.01)

| Treatment | No. traps | x̄♂/trap/day | ♂♂ |
|---|---|---|---|
| Attractant | 6 | 27.8 | 1,167 |
| Females* | 6 | 0.5 | 20 |

*One female per trap.

| Additional component | % | x̄♂/trap/day to Z5-14:Ac and E7-14:Ac at ratios of | | |
|---|---|---|---|---|
| | | 20:80+ | 11:89++ | 6:94+++ |
| None | — | 10.3 ab | 11.8 a | 2.8 ab |
| E5-14:Ac | 2 | — | 12.0 a | 4.0 a |
| | 6 | 9.2 ab | — | — |
| | 10 | — | — | 2.8 ab |
| E5-14:OH | 2 | — | 11.6*a | — |
| | 6 | 10.1 ab | — | — |
| | 15 | — | — | 3.4 ab |
| Z5-14:OH | 2 | — | 8.6*a | — |
| | 6 | 10.4 ab | — | — |
| Z7-14:Ac | 2 | 3.7 c | — | — |
| | 20 | 0.1 d | 0.0*b | — |
| Z7-14:OH | 12 | 1.5 e | — | — |
| E7-14:OH | 5 | — | 11.6 a | 3.0 ab |
| | 12 | 8.4 b | — | — |
| | 20 | — | 8.6 a | — |
| 14:Ac | 20 | 12.7 a | 10.9*a | 2.3**b |
| 14:OH | 20 | — | 9.0*a | — |
| 12:Ac | 20 | 13.0 a | 11.7*a | 2.0**b |
| 12:OH | 20 | — | 12.6*a | — |
| E5-14:Ac | 1 | } | | |
| Z5-14:OH | 1 | | — | 11.0 a | — |
| 14:Ac | 2 | | | |
| ♂♂ | | 5,532 | 10,097 | 1318 |

+ to +++ Means followed by the same letter did not differ (P > 0.05). Test periods and conditions were: +, Sept. 6-23 with traps 15 m apart; ++, Sept. 10 to 23 with traps 13 m apart; +++, Sept. 24 to Oct. 6 with traps 28 m apart and attractant at 1 mg/dispenser.
*and **The number of males attracted to these combinations with the 3rd component at 10% (*) or 30% (**) did not differ (P > 0.05).

| % Z7-14:Ac | Quantity (mg)/dispenser | ♂♂ |
|---|---|---|
| 0.0 | 0.2 | 720 |
| 4.4 | 0.2 | 7 |
| 8.4 | 0.2 | 3 |
| 0.0 | 1.0 }* | |
| 100.0 | 0.2 | 2 |

* Z5-14:Ac and E7-14:Ac were placed on 1 dispenser and Z7-14:Ac on another. Two dispensers were placed 1 cm apart in each trap.

| Third component | % | x̄♂/trap/day | ♂♂ |
|---|---|---|---|
| none+ | — | 11.1 | 639 |
| none* | 12.9 | 737 | |
| none** | — | 15.7 | 897 |
| none*** | — | 15.1 | 725 |
| E5-14:Ac+ | 2.7 | 15.2 | 868 |
| 14:Ac+ | 8.3 | 13.1 | 739 |
| 12:Ac+ | 8.3 | 14.9 | 847 |
| E5-14:Ac* | 2.7 | 14.4 | 811 |
| 14:Ac* | 8.3 | 12.5 | 707 |
| 12:Ac* | 8.3 | 12.6 | 719 |

+Z5-14:Ac and E7-14:Ac were synthesized (DLS) and purified (>99%) by argentation column chromatography followed by pglc.
*Z5-14:Ac and E7-14:Ac were synthesized by Raylo Chemical Co. and purified (>99%) in the same manner +.
**The chemicals were the same as * but pglc was omitted and purity was ca. 98%.
***The chemicals were the same as * but purified by distillation. Z5-14:Ac contained about 3% E5-14:Ac, 1% Z5-14:OH, 5% 14:Ac, and 4% 5$^a$-15:Ac. E7-14:Ac contained <1% E7-14:OH, <1% 14-Ac, and 5% 7$^a$-14:Ac.

| Additional components | % | x̄ ♂/trap/day | ♂♂ |
|---|---|---|---|
| none | — | 9.3 | 301 |
| none** | — | 10.6 | 370 |
| E5-14:Ac | 0.4 | 5.4 | 190 |
| 14:Ac | 1.8 | 6.9 | 245 |
| E5-14:Ac, 14:Ac | 0.4, 1.8 | 9.6 | 318 |
|  | 0.4, 5.2 | 7.5 | 248 |
|  | 0.8, 9.8 | 6.0 | 208 |
| 5$^a$-14:Ac | 5.2 | 6.0 | 207 |
| 7$^a$-14:Ac | 5.2 | 6.3 | 233 |
| E5-14:Ac, 14:Ac | 0.4, 1.8 } |  |  |
| 5$^a$-14:Ac, 7$^a$-14:Ac | 5.2, 5.2 | 9.3 | 302 |

*Chemicals from Raylo Chemical Co. purified (>99%) by argentation column chromatography followed by pglc.
**The same chemicals as * except pglc was omitted and purity was ca. 98%.

Table 10

| Combinations Tested | Ratios | Total Males Caught |
|---|---|---|
| Z5-14:Ac/E7-14:Ac | 5:95 | 208 |
| Z5-14:Ac/E11-14:Ac | 5:95 | 117 |
| Z5-14:Ac/E7-13:Ac | 5:95 | 33 |

Table 10-continued

| Combinations Tested | Ratios | Total Males Caught |
|---|---|---|
| Z5-14:Ac/Z7-13:Ac | 95:5 | 34 |
| Z5-14:Ac/Z7-13:Ac | 5:95 | 0 |
| Z5-14:Ac/E7-14:Ac/E11-14:Ac | 5:95:40 | 204 |
| Z5-14:Ac/E7-14:Ac/E11-14:Ac | 1:5:10 | 119 |
| Z5-14:Ac/E7-14:Ac/E7-13:Ac | 5:95:40 | 145 |
| Z5-14:Ac/E7-14:Ac/E7-13:Ac | 5:95:2 | 72 |
| A5-14:Ac/E7-14:Ac/Z7-13:Ac | 5:95:2 | 42 |

We claim:

1. An attractant composition for male moths of the army cutworm *Euxoa auxiliaris* (Grote) comprising (a) Z-5-tetradecen-1-yl acetate and (b) E-7-tetradecen-1-yl acetate in ratios of (a)/(b) within the range of about 1/99 to about 20/80.

2. The attractant of claim 1 wherein the range of (a)/(b) is from about 5/95 to about 10/90.

3. The attractant of claim 1 including the compound E-11-tetradecen-1-yl acetate in amounts up to about 50% of (b).

4. The attractant composition of claim 1 in conjunction with a liquid or solid carrier.

5. The attractant composition of claim 1 in combination with a rubber carrier.